(12) United States Patent
Delacourte et al.

(10) Patent No.: US 7,723,117 B2
(45) Date of Patent: May 25, 2010

(54) MEANS FOR DETECTING PATHOLOGICAL TRANSFORMATION OF THE APP PROTEIN AND THEIR USES

(75) Inventors: André Delacourte, Faches-Thumesnil (FR); Nicolas Sergeant, Ronchin (FR); Dorothée Vanuxeem, Lambersart (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1551 days.

(21) Appl. No.: 10/415,479

(22) PCT Filed: Nov. 5, 2001
(Under 37 CFR 1.47)

(86) PCT No.: PCT/FR01/03410

§ 371 (c)(1),
(2), (4) Date: Jun. 15, 2004

(87) PCT Pub. No.: WO02/37118

PCT Pub. Date: May 10, 2002

(65) Prior Publication Data

US 2007/0026527 A1  Feb. 1, 2007

(51) Int. Cl.
*G01N 33/50* (2006.01)
*G01N 33/48* (2006.01)
*G01N 33/00* (2006.01)

(52) U.S. Cl. .................... 436/86; 435/7.2; 435/7.1; 435/4

(58) Field of Classification Search ............... 435/7.21, 435/70.1, 7.2, 7.1, 4; 436/86
See application file for complete search history.

(56) References Cited

U.S. PATENT DOCUMENTS 5,234,814 A    8/1993  Card et al.
6,114,133 A *  9/2000  Seubert et al. ............ 435/7.94

FOREIGN PATENT DOCUMENTS

EP    A0564946    10/1993
WO    WO94/07144   3/1994

* cited by examiner

*Primary Examiner*—Walter D Griffin
*Assistant Examiner*—Christine T Mui
(74) *Attorney, Agent, or Firm*—Buchanan Ingersoll & Rooney PC

(57) ABSTRACT

Pathological modifications of the APP protein can be detected in a sample by use of markers consisting of catabolic and/or metabolic fragments of the carboxyl-terminal part of the APP (APP-Cter fragments) resulting from a neurodegenerative condition wherein the APP participates in the etiology. Methods for detecting such markers provide diagnostic and therapeutic applications in degenerative pathologies such as Alzheimer's Disease.

26 Claims, 16 Drawing Sheets

Figure 1:
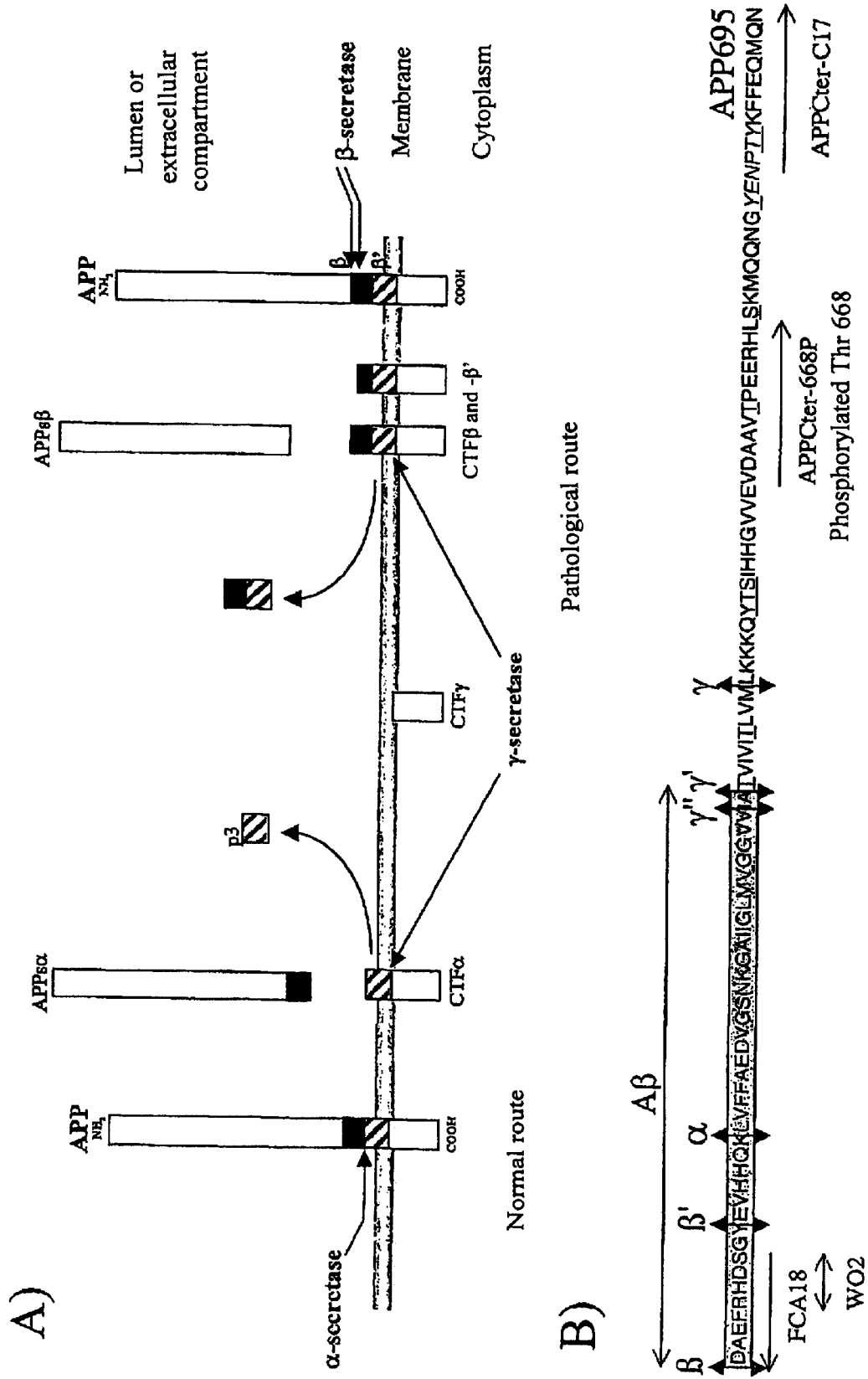

Figure 6
Mouse cerebral tissue
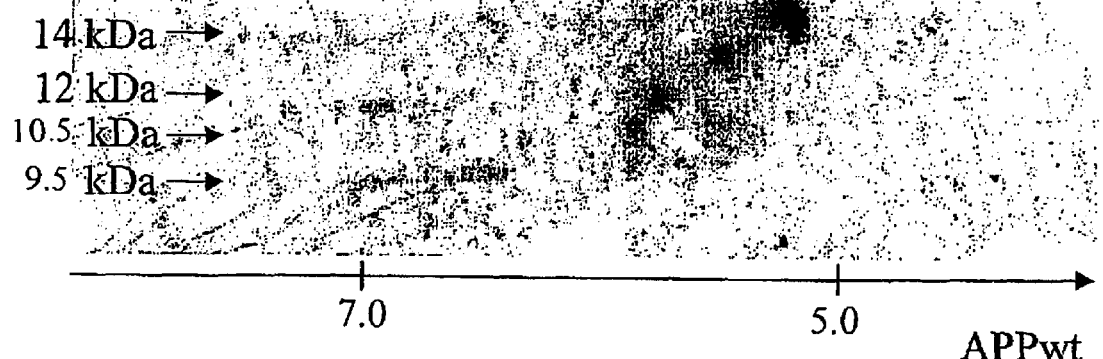
Control
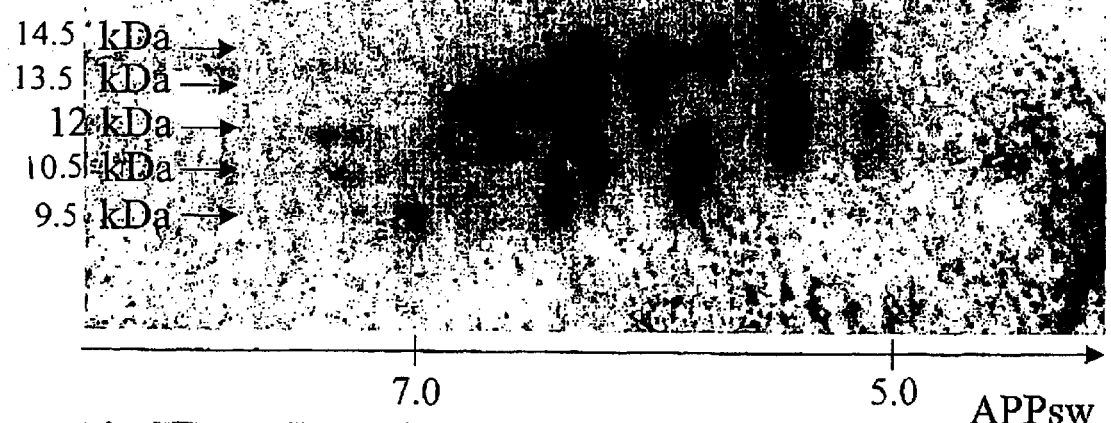
APPwt
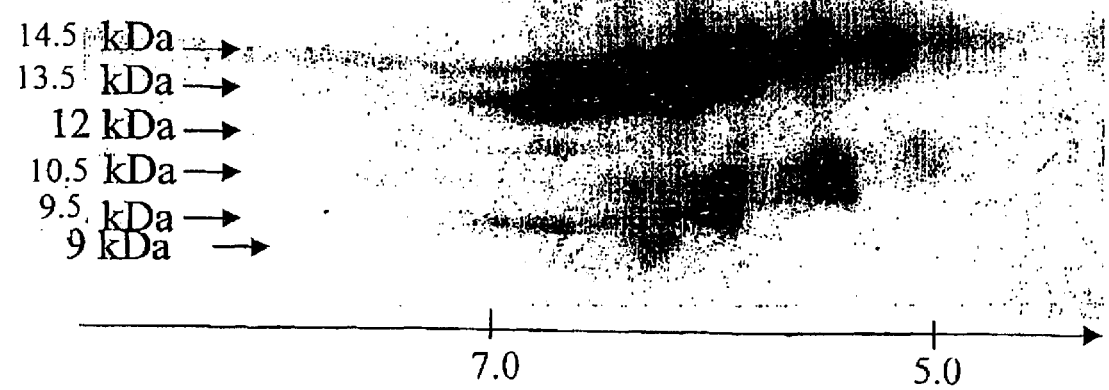
APPsw Figure 10
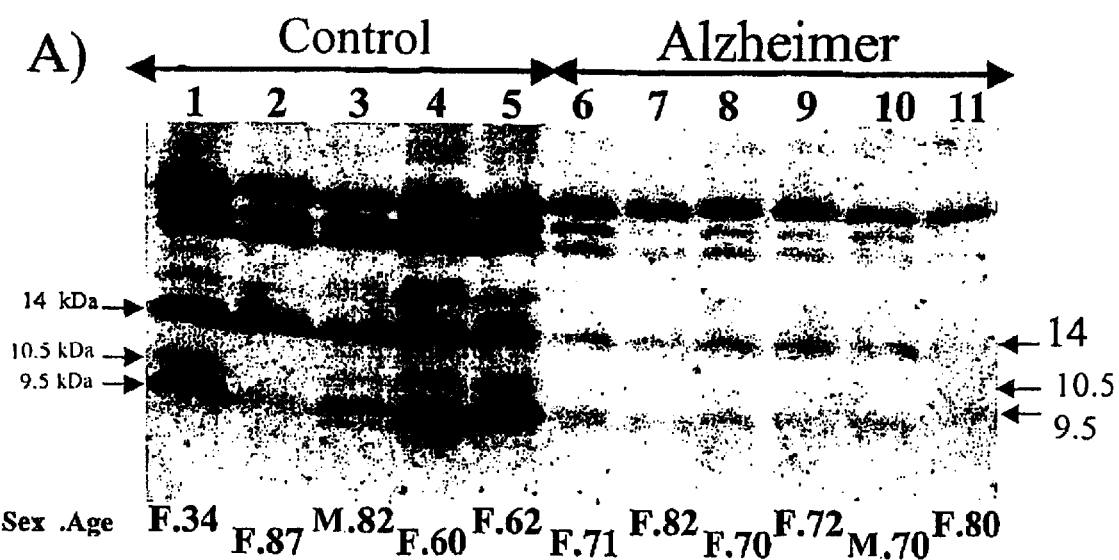
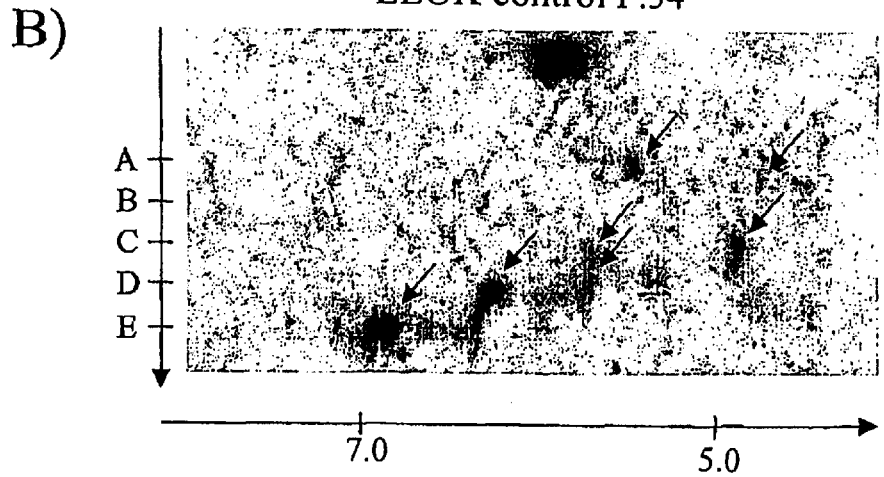

Figure 14

| APP-Cter fragments which disappear in Alzheimer's Disease |||||||
|---|---|---|---|---|---|---|
| APP-Cter | Molecular Mass | Isoelectric points ||||||
| A | 15.0 kDa |  |  | 5.37 | 5.13 |  |
| A | 14.5 kDa | 5.95 | 5.64 |  |  |  |
| B | 13.5 kDa |  |  | 4.94 | 4.80 |  |
| B | 12.7 kDa | 5.90 | 5.29 |  |  |  |

| APP-Cter fragments specific to Alzheimer's Disease |||||||
|---|---|---|---|---|---|---|
| APP-Cter | Molecular mass | Isoelectric points ||||||
| D | 11.0 kDa |  |  |  | 4.94 |  |
| D | 10.5 kDa | 7.5 |  | 5.35 |  |  |
| E | 9.5 kDa |  | 5.77 |  |  |  |

| APP-Cter fragments common to the pre-clinical forms and to Alzheimer's Disease |||||||
|---|---|---|---|---|---|---|
| APP-Cter | Molecular mass | Isoelectric points ||||||
| A | 15 kDa |  |  |  | 4.55 |  |
| B | 14.0 kDa |  |  | 5.37 | 5.2 |  |
| C | 12.7 kDa |  |  | 5.64 | 5.45 |  |
| D | 10.5 kDa | 6.05 | 5.91 |  |  |  |

Figure 15

| APP-Cter fragments of the control human lymphocytes | | | | | | | |
|---|---|---|---|---|---|---|---|
| | | Isoelectric points | | | | | |
| APP-Cter | Molecular mass | | | | | | |
| A | 14 kDa | | | 5.45 | 4.85 | | |
| C | 12.0 kDa | | 5.64 | | 4.96 | | |
| D | 10.5 kDa | | 5.77 | | | | |
| | 10 kDa | 6.25 | | | | | |
| E | 9.5 kDa | 6.99 | | | | | |
| | | | | | | | |
| APP-Cter fragments of the Alzheimer's human lymphocytes | | | | | | | |
| | | Isoelectric points | | | | | |
| APP-Cter | Molecular mass | | | | | | |
| A | 14.5 kDa | | | 5.45 | | | |

Figure 16

| APP-Cter | | Isoelectric points | | | | | |
|---|---|---|---|---|---|---|---|
| APP-Cter fragments of transgenic mice and different from the endogenic APP-Cter fragments ||||||||
| APP-Cter | Molecular mass | | | | | | |
| A | 18 kDa | 5.91 | 5.77 | 5.54 | 5.37 | 5.20 | 5.13 |
|   | 17.5 kDa | 6.20 | 5.91 | | | | |
|   | 16 kDa | 6.20 | 5.91 | 5.64 | 5.37 | 5.13 | 4.55 |
|   | 14.5 kDa | | 6.80 | 6.60 | 6.36 | 6.20 | 5.91 |
| B | 13.5 kDa | | | | | 6.36 | 6.20 |
|   | 13.0 kDa | 6.70 | 6.63 | 6.40 | 6.27 | 6.15 | 5.10 |
| C | 12.0 kDa | | 7.50 | 6.20 | 5.91 | 5.37 | 5.00 |
| D | 10.5 kDa | | | | | 7.40 | 5.37 |
| E | 9.5 kDa | 6.75 | 6.63 | 6.50 | 6.25 | 6.15 | 6.00 |

MEANS FOR DETECTING PATHOLOGICAL TRANSFORMATION OF THE APP PROTEIN AND THEIR USES

The invention relates to means for detecting the pathological transformation of the APP protein (Amyloid Precursor Protein) in neurodegenerative diseases such as Alzheimer's disease.

It relates more particularly to a method for detecting such a transformation, kits for its implementation, as well as its therapeutic and diagnostic uses.

Alzheimer's disease (AD) is a neurodegenerative disease which leads to the loss of intellectual functions and therefore to the progressive and irreversible onset of dementia. This disease is set to present a major problem in the future, with the ageing of the population, as age is the major risk factor.

99% of the forms observed are non-familial. For the familial autosomal dominant forms, the pathological mutations are observed on the APP gene of chromosome 21, and on the PS1 and PS2 (presenile 1 and 2) genes which are found on chromosomes 14 and 1.

Two degenerative processes characterize Alzheimer's disease. Amyloidogenesis, which results from a dysfunction of the APP protein, and neurofibrillary degeneration (NFD), which corresponds to the accumulation of tau protein in the nerve cells.

The dysfunction of the APP protein lies at the very origin of Alzheimer's pathology, but the precise cause of the neuronal degeneration and death are not yet known.

Two hypotheses have been put forward. According to the first hypothesis, which is the most widespread, the cleavage product of the APP, the Aβ peptide, with 39 to 43 amino acid residues, is neurotoxic and responsible for the NFD chain reaction.

According to the second hypothesis, the degeneration results from a loss or gain in the APP function, which is translated in parallel and secondarily by an accumulation of the Aβ peptide in the form of amyloid plaques.

Amyloidogenesis modelling is possible thanks to transgenic mice with mutated APP or APP+PSI genes. These mice progressively develop amyloid plaques, but no NFD is observed. These mice are already used by the pharmaceutical industry to test molecules capable of inhibiting the formation of the Aβ peptide. The principal strategy consists of blocking the enzymes responsible for producing the Aβ peptide. The enzymes of this type known at present are the β and γ secretases (1).

Molecules which become fixed onto the amyloid deposits are also tested. These are breakers of the β structures (β sheet breakers) or anti-amyloids (2).

Vaccination against the amyloid peptide is also in the process of evaluation (3).

At the present time, no significant and confirmed modification of the APP protein in human tissue affected by Alzheimer's disease has been discovered, other than the increase in the production of the 1-42 Aβ peptide, the increase in the 1-42/1-40 Aβ ratio, and its aggregation in the form of insoluble deposits and amyloid plaques.

A modification of the secretion of the N-terminal part of the APP, known as sAPP, has also been reported in in vitro tests of the 715 mutation on the APP (4).

The research carried out by the inventors has led them to observe significant modifications of the APP protein which are not linked to the detection of the Aβ peptides, and which are specifically detectable in Alzheimerized human tissue, and in the experimental models.

These modifications are demonstrated in the human tissue (central nervous system, peripheral liquids and tissues) affected by Alzheimer's disease, as well as in other neurodegenerative pathologies with APP dysfunction.

The significant modifications are both qualitative and quantitative and they are detected upstream of the production of the Aβ peptide.

Similar anomalies can be found in large quantities in transgenic mice with pathological mutations on the APP or mutated APP+mutated presenile 1.

The invention therefore relates to the use of these modifications observed in human cerebral tissue as markers in a method for detecting the pathological transformation of APP, in particular in a neurodegenerative process.

It relates to the use of these markers in particular for the diagnosis and monitoring of a neurodegenerative process, the development of animal models and the screening of medicaments effective against the APP pathologies.

The invention also relates to a method for evaluating said pathologies comprising the definition of an index established with respect to a system of reference.

The method for detecting, in a sample to be analyzed, pathological modifications of the APP protein, is characterized in that markers are used, constituted by catabolic and/or metabolic fragments of the carboxy-terminal part of the APP, hereafter called APP-Cter fragments, specifically modified in neurodegenerative pathological situations where the APP participates in the etiology.

The studies carried out by the inventors have shown that, in an unexpected manner, the modifications involving such fragments were directly linked to the onset and progression of the degenerative process in the cerebral regions, in particular in the case of Alzheimer's disease.

It is observed that the fragments in question are catabolic and/or metabolic products of the APP which have retained the primary structure of the C-terminal end of the APP and can therefore be recognized by an antibody to this C-terminal part of the APP.

The term "fragment" as used in the description and the claims therefore encompasses the charge and isoelectric point variants which are different due to post-translational modifications, such as for example phosphorylation and/or methylation and/or acetylation and/or glycosylation, to the extent that these variants are recognized by an anti-APP-Cter antibody as described in the examples.

These are in particular fragments as identified by biochemical analysis of a sample to be analyzed, by 1-D electrophoresis (one-dimensional electrophoresis) or 2-D electrophoresis (two-dimensional electrophoresis) coupled with immunoblotting and revelation by a set of anti-APP-Cter polyclonal and/or monoclonal antibodies, and in addition by a set of antibodies to the post-translational modifications of the pathological transformation of the APP-Cter.

The electrophoresis can be one- and/or two-dimensional.

Such fragments are specifically modified in the pathological tissues. The reduction, even disappearance, of certain of these fragments with the progression of the neurodegenerative process is noted. In parallel, a modification of the electric charge of certain of these fragments and a modification of their solubility is noted.

The invention especially relates to the use of this method for diagnosing the Alzheimerization process, and thus refers to the use, as APP dysfunction markers, of 5 major fragments which are modified in the process of Alzheimerization, the molecular weights of which, determined by one-dimensional (1-D) electrophoresis are 14.5; 13.5; 12; 10.5 and 9.5 kDa. For convenience, these fragments are designated by the letters A, B, C, D, E. It is to be noted that a band of 9 kDa (F) is also present and a band of 6.5 kDa, in smaller and variable quantities.

The variants which disappear correspond to the 1-D electrophoretic band of 14.5 kDa, designated A, divided into two components of 15 kDa and 14.5 kDa in 2-D, with isoelectric variants of isoelectric points of 5.13 (represented by 15/5.13) and 15/5.37 for the 15 kDa component and 14.5/5.64 and 14.5/5.95 for the other component. There is also the disappearance of fragments corresponding to the electrophoretic band B of 13.5 kDa which is divided into two components of 13.5 and 12.7 kDa, with the isoelectrical variants 13.5/4.94 and 12.7/4.8; 12.7/5.29.

Useful fragments are also modified in the early stage of Alzheimer's disease. They correspond to the electrophoretic variants 15/4.55; 14/5.2; 14/5.37, 12.7/5.45; 12.7/5.64; 10.5/5.91; 12.7/6.05. These variants are particularly informative to the extent that they are early markers.

The fragments which appear during Alzheimerization correspond to the 1-D electrophoretic band of 10.5 kDa, divided into two components of 11 kDa and 10.5 kDa in 2-D, with isoelectric variants 11/4.94; 10.5/5.35 and 10.5/7.5 and the fragment of 9.5 kDa and of pI 5.77.

In parallel, modifications of solubility of the APP-Cter markers are also observed during the evolution of the pathological process of neurodegeneration. The fragments of 14.5 and 13.5 see their solubility reduce and the fragments of 10.5 and 9.5 see their solubility increase during the Alzheimerization of the cerebral tissue.

Such fragments are modified in the tissues or cells described as "alzheimerized". They can be modified in a similar manner in experimental models, such as transgenic animals carrying a mutated or non-mutated gene or combination of genes, involved in Alzheimer's pathology.

It is noted with interest that these differences in catabolism and metabolism of the APP protein, as observed with the APP-Cter markers, are observed in the neuronal cellular models (for example the neuroblastoma cells such as the SKNSH SY5Y strain, the NT2 strain, the Kelly strain), the glioblastoma strains (CCF, U118, T98), but also in the non-neuronal cells, such as the CHO, COS, HT-29 and Hela strains.

It is also noted that each cell line naturally possesses its own particular pattern of expression of these fragments (variation of the overall quantity of the fragments of molecular mass 13.5; 12; 10.5; 9.5; 9; 8.5 and 6.5 kDa expressed with respect to the total proteins of the cellular model; variations of the relation between each fragment.

For these models, and in a manner specific to each model, the expression of the fragments A-F is also modified depending on the state of differentiation of the cell strains.

These variations are also observed in the animal models, in particular in the transgenic mice with the possible different constructions (APP mutations and/or PS1 or PS2 mutations and/or absence of PS1 expression) and/or mutated or non-mutated tau gene (14.5; 13.5; 12; 10.5; 9.5; 9; 8.5 and 6.5 kDa). The samples to be analyzed, used in said method therefore comprise both neuronal tissues or cell strains, and non-neuronal tissues or cell strains, for example biological liquids such as cephalo-rachidian liquid, blood and all or part of its formed elements, which facilitates an early diagnosis, evaluation of the risk factors in a patient, or therapeutic monitoring.

These tissues are advantageously homogenized or fractionated, for example by centrifugation, with a view to their use in the detection method.

The above method is also used for the differential diagnosis of neurodegenerative pathologies related to Alzheimer's disease, such as dementia with Lewy bodies or the amyloid angiopathies.

The detection method defined above makes it possible to define an index of transformation of the APP protein to pathological protein.

The invention relates in particular to a method of evaluation of a neurodegenerative pathological process in a sample to be analyzed, by immuno-chemical analysis, as described in the examples, characterized in that an index is allocated to the fragments identified in the sample studied, with respect to a system of reference where the index 0 (zero) corresponds to detection in healthy tissue, and the index 100 (one hundred) in pathological tissue, either human, from transgenic mice with gene mutations implicated in Alzheimer's pathology, or native cell strains, or transfected with said genes.

Such an index has a diagnostic and therapeutic advantage. It makes it possible to rapidly reflect the pathological state. The value of the index in fact makes it possible to determine whether there is a risk of developing Alzheimer's disease. Obtaining a high index can help to back up a clinical diagnosis.

Moreover, within the scope of a therapeutic treatment based on the catabolism and metabolism of APP or its correction, the modifications of such an index make it possible to monitor the effect of the treatment.

It constitutes a reference making it possible to compare the effect of different molecules against Alzheimer's disease or other neurodegenerative pathologies, a modification of the index demonstrating the effectiveness of the molecules tested and the potentialities of their therapeutic usefulness.

Such an index also has a use in analyzing the early etiological events responsible for the disease, leading to the discovery of effective new molecules, as well as to the development of new therapeutic strategies.

It is also noted that this index can be used in order to slow down or even to induce a degeneration in order to establish new experimental models. This index can also provide information making it possible to cause a targeted degeneration within the scope of therapeutic actions requiring the disappearance of a precise cell population.

The method according to the invention can advantageously use in addition a set of polyclonal and/or monoclonal antibodies in order to reveal post-translational modifications of the pathological transformation of the APP-Cter fragments, in particular a phosphorylation and/or methylation and/or acetylation and/or glycosylation-type modification.

Preferably, the set of polyclonal and/or monoclonal antibodies used makes it possible to reveal the phosphorylations and the variation of expression of the fragments of 14.5; 12 and 10.5 kDa.

The detection method according to the invention can advantageously be used in order to establish and validate experimental models, cells or animal models of Alzheimer's disease. The relevant models reproduce the modifications of the APP-Cter fragments as observed in human tissue, as described in the examples.

It also makes it possible to help set up effective therapeutic tests by improving patient selection.

Another use of considerable interest relates to pharmacological screening for the selection of medicaments effective against Alzheimer-type neurodegenerative pathologies. Thus, the molecules selected are characterized in that they are capable of modifying the Alzheimer profile referred to above, by leading to a restoration of the properties of the APP-Cter markers, or to a restoration of their physico-chemical properties (solubility, electric charge).

The invention therefore makes it possible to carry out rapid and relevant pharmacological screening of useful molecules.

The invention also relates to a kit for the diagnosis of the pathological transformation of APP, characterized in that it comprises a set of polyclonal and/or monoclonal antibodies to the carboxy-terminal region of the APP. The use of a set of antibodies to the post-translational modifications linked to the pathological transformation situated on APP-Cter fragments, such as for example sites of phosphorylation, methylation, acetylation or glycosylation on these fragments can advantageously provide additional information about the demonstration and quantification of the pathological transformation of the APP-Cter fragments.

The heterogeneity of the APP-Cter fragments demonstrated by the 2-D electrophoreses is explained in part by the phosphorylation modifications, as demonstrated by a phospho-dependant polyclonal antibody to phosphorylated threonine 668 (nomenclature with APP 695), situated in a region common to the APP-Cter fragments.

They also result from glycosylation, as shown by the anti-glycosylation drugs which modify the profile of the APP-Cter fragments. Methylation and acetylation are two post-translational modifications which are also involved in the pathological transformation of the APP-Cter fragments. In fact, they are essentially localized on lysine residues, which causes acidification and therefore a change in isoelectric point.

They are also the outcome of a control by genes involved in Alzheimer's disease. It is in this way that the overexpression of the Tau protein is capable of influencing the ratio of the 13.5; 9.5 and 6.5 kDa bands.

These antibodies can be used in an immuno-chemical assay for example in ELISA, Western blot, dot blot. The kits according to the invention therefore advantageously contain the elements necessary for carrying out such assays.

Figure 11:
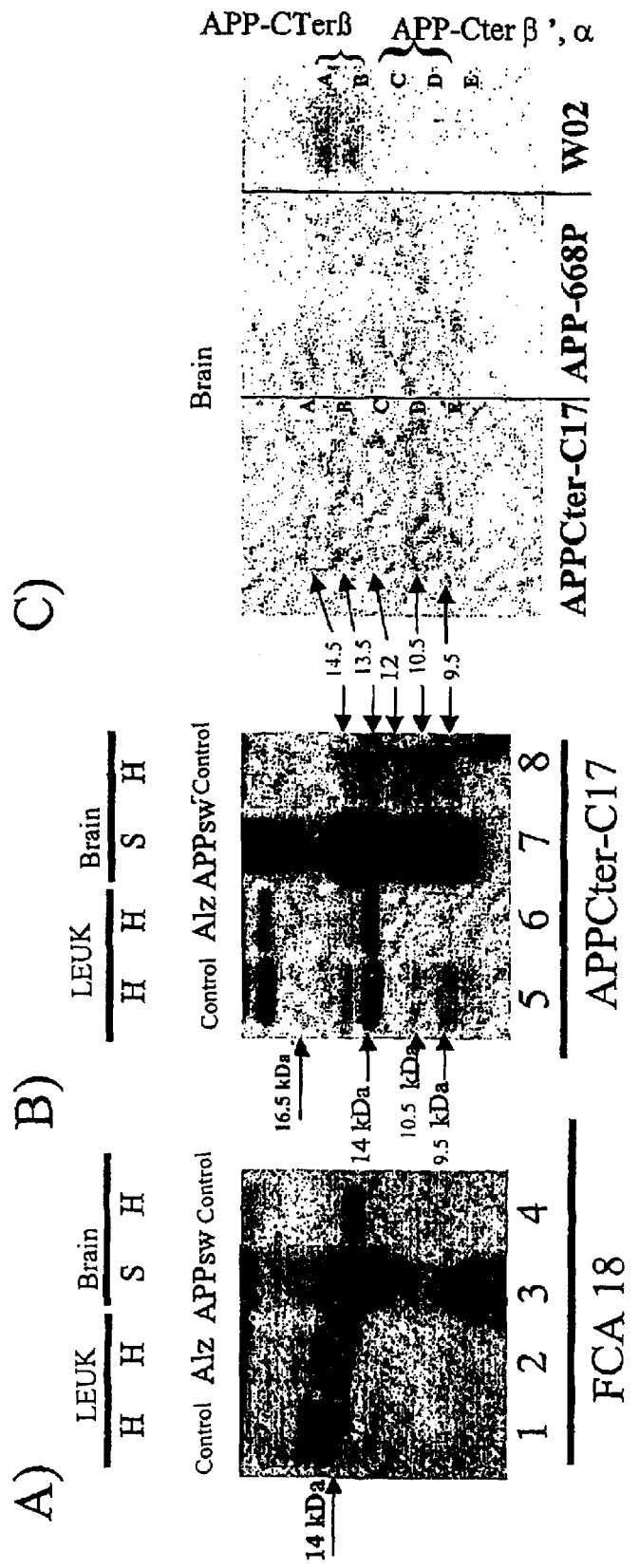
Figure 12:
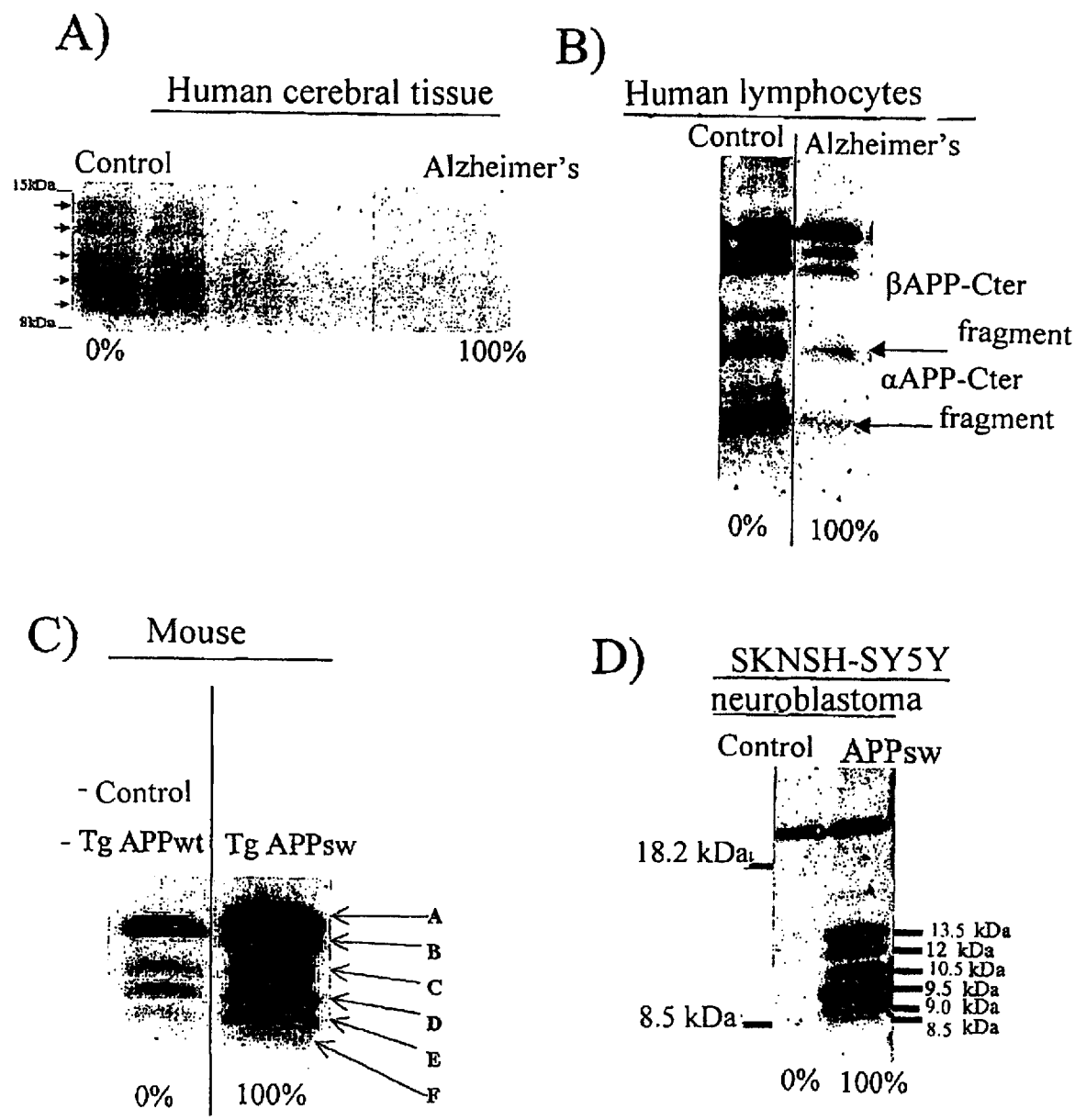
Figure 13:
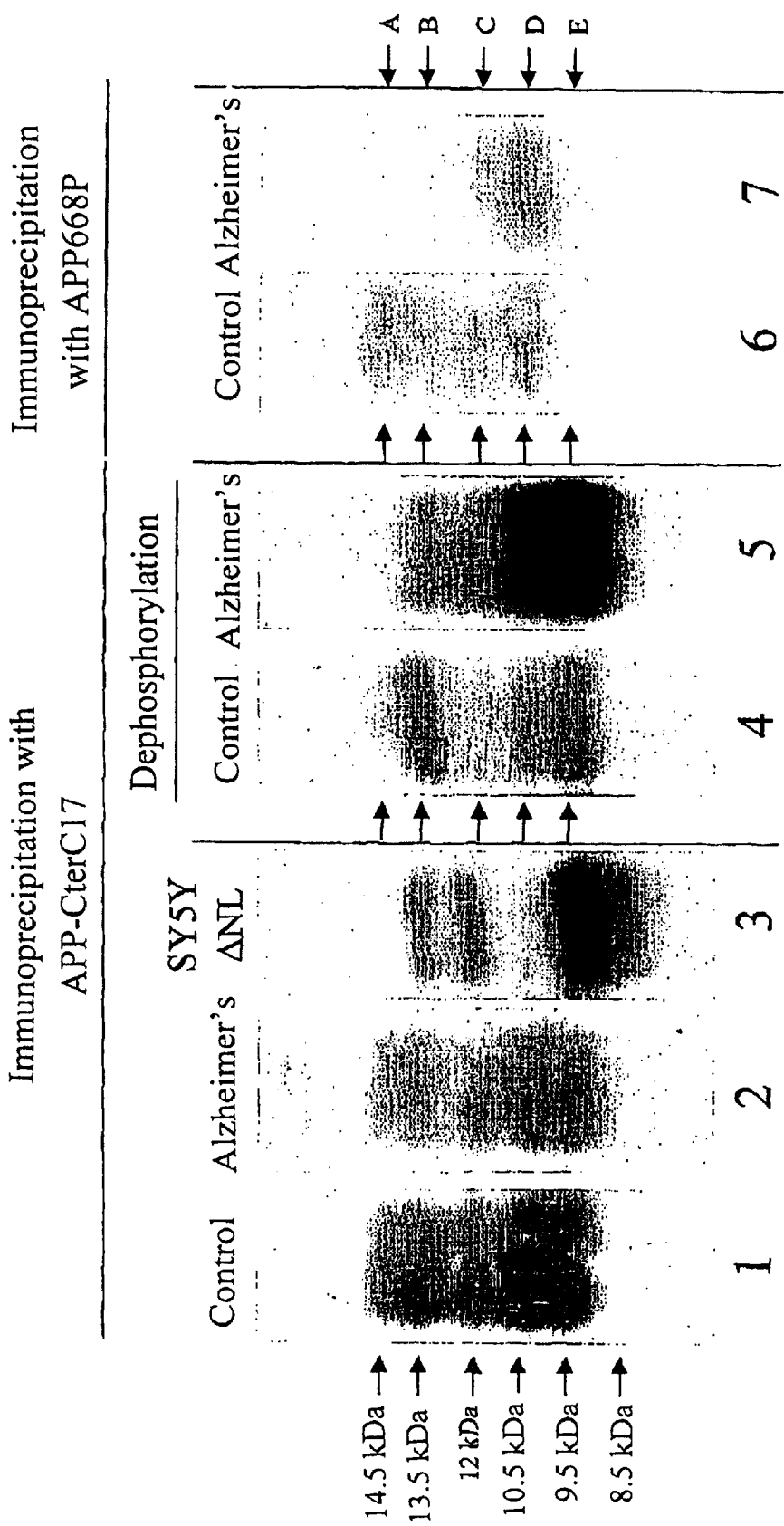

Other characteristics and advantages of the invention will appear in the examples which follow, with reference to FIGS. 1 to 16, which represent, respectively, the theoretical diagram of cleavage of the APP-Cter fragments and localization of the epitopes of the antibodies used (FIG. 1)

the Western blot photos of human cerebral tissue (1-D) (FIGS. 2A to 2B), and assay of the APP-Cter fragments (FIGS. 2C and 2D), fractionation of the human cerebral tissue (FIGS. 3A and 3B), human cerebral tissue (2-D) (FIGS. 4A to 4C), cerebral tissue of transgenic mice (1-D) (FIGS. 5A and 5B), cerebral tissue of mice (2-D) (FIG. 6), a synthesis of the 2-D profiles of APP-Cter fragments in the mice, human cerebral tissue and human lymphocytes (FIGS. 7A, 7B, 7C respectively), the Western blot photos of cerebral tissue of WT and SW mice, non-neuronal cell strains with APP wt and sw (FIG. 8), comparison of the human cerebral tissue with the neuronal-type cell strains transfected or not transfected with APP wt, sw, mutated PS1, 3R or 4R Tau (FIG. 9), human lymphocytes: 1-D and 2-D analyses (FIGS. 10A and 10B), the characterization of the APP-Cter fragments with anti-Aβ-N-terminal antibodies, APP-Cter and a phospho-dependent APP-Cter antibody (FIG. 11)

the pathological transformation index (FIGS. 12 A to D)

the influence of phosphorylation on the pathological transformation of the APP-Cter's (FIG. 13)

summary tables of the variants according to the invention (FIGS. 14 to 16).

MATERIALS AND METHODS

Antibodies

Production of the APP-Cter-C17 Polyclonal Antibody

A polyclonal antibody to the carboxy-terminal part of the APP was produced according to the immunization protocol described by Vaitukaitis et al, (5). New Zealand rabbits were immunized with a 411 peptide comprising the last 17 amino acids of the human APP sequence, corresponding to its carboxy-terminal end. The peptide was coupled by covalence to ovalbumin. 200 μg of immunogen were injected every two weeks. Before the injection, 1 volume of Freund's complete adjuvant was added to the immunogen solution, at the time of the first booster and the following boosters, with Freund's incomplete adjuvant in place of the complete adjuvant. The blood was taken one week after the 4th injection and one week after each following injection. The pure serum was obtained after coagulation of the blood and centrifugation for 10 minutes at 2000 g. 1 volume of glycerol was added to the serum and the mixture was stored at −20° C.

Purification of the APP-Cter-C17 Antibody 1 mg of peptide used for the immunization was coupled to a NHS-Fast Flow Sepharose® matrix (Amersham Pharmacia Biotech) according to the manufacturer's instructions. The coupled matrix was brought into contact with 200 μl of pure serum diluted in one volume of 2× binding buffer (50 mM Tris pH 8.0; 300 mM NaCl and 0.1% (v/v) of Tween-20) and gently stirred overnight at 4° C. All of the solutions were passed over a PD-10 column. The matrix was washed with 10 volumes of the binding buffer. The purified antibody was eluted with 2 volumes of acetate buffer at pH 3.5. The protein concentration was determined using Pierce's BCA protein quantification kit.

Production of the APP-668P Polyclonal Antibody

An antibody to a synthetic peptide corresponding to the Val-Asp-Ala-Ala-Ala-Val-(phosphorylated)Thr-Pro-Glu-Glu-Arg-His-Leu sequence was produced, following the same protocol as that used for the APP-Cter-C17. This antibody recognizes the immunogen, but it does not recognize a peptide having the same sequence, but not phosphorylated.

Samples

Samples of Human and Murine Cerebral Tissue

The human cerebral tissue originates from patients who have been monitored prospectively, and described in (6) The cerebral tissue samples, obtained after autopsy or biopsy and stored at −80°, were dissected using an anatomical atlas, then homogenized with a Teflon® potter in 10 volumes of 1×1-D lysis buffer (50 mM Tris-HCl pH 6.8; 4 mM EDTA; 5% (w/v) of SDS, 10% (v/v) of glycerol, 2% (v/v) of β-mercaptoethanol and 0.05% of Bromophenol Blue) for a 1-D analysis. The samples were taken to 100° C. for 10 minutes, then maintained at −80° C. until used. For a 2-D analysis, the tissue is homogenized in a 10 mM Tris-HCl pH 6.8 buffer, then one volume of 2×2-D buffer (7M urea; 2M thiourea; 0.4% Pharmalytes® 3-10 (w/v); 8% (v/v) Triton X-100; 10 mM of dithiothreitol; 0.1% Bromophenol Blue) is added to it, and it is stored at −80° C. until used. For the rodent cerebral tissue samples, the brain was rapidly removed after the death of the animal and treated in the same manner as the human samples.

Murine Lines Used

Murine cerebral tissue samples were prepared following the same protocol as for the human cerebral tissue samples. Cerebral tissue samples from non-transgenic mice and transgenic mice with the wild-type human APP gene (APPwt) or the human APP gene mutated at codons 670 and 671 (APPsw). This mutation of the APP is linked with a familial form of Alzheimer's disease, known as Swedish mutation (7). Other samples were also used, comprising non-transgenic mice, and different lines of transgenic mice with the APPwt and APPsw gene. A sample of murine cerebral tissue similar to the transgenic mouse developed by Hsiao K. et al. (8) was also used.

Samples of Cerebral Tissue after Protein Fractionation

The cerebral tissue samples were homogenized according to a ratio of 1/10 (w/v) in 10 mM Tris-HCl pH 6.8 buffer then centrifuged at 100,000 g for one hour at 4° C. The supernatant (F1) was retained and the pellet re-homogenized in the same buffer with 0.5% (v/v) of Triton X-100 added to it. After centrifugation, the soluble Triton X-100 fraction, named F2 fraction, is stored. An additional stage of extraction and centrifugation in the same buffer was carried out under the same conditions, which produces the F2' fraction. The pellet is then rapidly taken up in the 1-D lysis buffer (see below) and corresponds to the F3 fraction.

According to the biochemical technique used, at the time of use, the following corresponding buffers were added to the supernatants: 1 volume of 2×1-D lysis buffer (100 mM Tris-HCl pH 6.8; 8 mM EDTA; 10% (w/v) of SDS; 20% (v/v) of glycerol; 4% (v/v) of β-mercaptoethanol and 0.1% (v/v) of Bromophenol Blue) for a one-dimensional (1-D) electrophoresis study or 1 volume of 2-D lysis buffer (7M urea; 2M thiourea; 0.4% Pharmalytes® 3-10 (w/v); 4% (v/v) Triton X-100; 10 mM of dithiothreitol; 0.1% Bromophenol Blue) for a two-dimensional (2-D) electrophoresis study.

Immunoprecipitation

The F2 fraction is used in order to immunoprecipitate the APP-Cter fragments. 100 µl of the F2 fraction are diluted in 300 µl of mM Tris HCl pH 7.4 buffer containing 1% of NP.40 (immunoprecipitation buffer). 10 µl of APP-Cter-C17 or APP668P antibodies are added and the mixture is incubated under stirring overnight at 4° C. 40 µl of protein A fixed on agarose beads (Pierce) are added to the solution and the mixture is incubated under stirring at 4° C. for one hour. The agarose beads are washed three times in the immunoprecipitation buffer then the APP-Cter fragments are released by a treatment with 50 µl of SDS buffer and recovered in the centrifugation supernatant. The APP-Cter fragments are then analyzed by immunoblotting after electrophoresis on Tris-Tricine gel.

Samples of CHO (Hamster) or SKNSH SY5Y (Human) Cell Cultures

The cells are transfected in a stable manner with the wild-type human APP gene or the human APP gene carrying the Swedish mutation. The pellet of cells was taken up in a 10 mM Tris-HCl 6.8 buffer then subjected to ultrasound. Before use, 1 volume of lysis buffer is added to the sample, corresponding to the 2× (1-D or 2-D) experiment. In the case of a 1-D analysis, the sample is taken to 100° C. for 10 minutes.

Samples of Human Leukocytes

Preparation of human leukocytes: 10 milliters of blood are collected in EDTA (ethylene diamine tetra-acetate) tubes. Centrifugation is carried out at 4500 rpm (revolutions per minute) for 15 minutes. The plasma is eliminated. The tube is two-thirds filled with a solution for lysis of the erythrocytes (lysis solution: 0.91 mM $NH_4CO_3$, and 0.132 mM $NH_4Cl$). The tube is stirred delicately and it is placed in a water bath refrigerated at 5° C. Centrifugation is carried out at 4000 rpm for 15 minutes and the supernatant is eliminated. The pellet of leukocytes is rinsed twice with the lysis solution following the same methodology. The pellet is then drained, and it is either used within 24 hours, or frozen at −20° C. for its transport or later use.

The pellet of leukocytes is taken up in a 10 mM Tris-HCl pH 6.8 buffer then subjected to ultrasound. Before use, 1 volume of 2× lysis buffer is added to the sample, corresponding to the (1-D or 2-D) experiment. In the case of a 1-D analysis, the sample is taken to 100° C. for 10 minutes.

Electrophoretic Techniques

1-D Electrophoresis

The experiments were carried out using the Protean IIXi Cell electrophoresis system (Biorad) according to the manufacturer's instructions.

The 1-D electrophoreses were carried out according to the protocols described by Laemmli (9) for the production of the gel and under the migration conditions described by Schäger and Von Jagow (10). The concentration gel contains 4% of acrylamide and the separation gel used contains 16.5% of acrylamide. The migration takes place in Tris-Tricine buffer. The migration programme used is as follows: 1 hour at 30 V constant then 16 hours at 45 mA.

Each well was loaded with an equivalent quantity of protein (approx. 100 µg/well).

2-D Electrophoresis

1st Dimension

The first dimension or focusing is carried out using pre-cast gel strips known as IPG Strip® covering a gradient of pH 3-10, according to the constructor's instructions. The material used for the isoelectric focusing is the Protean IEF Cell system (Biorad).

1× rehydration buffer (7M urea, 2M thiorea, 4% triton X100; 0.5% CHAPS; 0/2% (w/v) Pharmalytes® pH 3-10; 10 mM DTT; 0.01% orange G) is added to a quantity of 250 µg of proteins in order to have 400 µl to apply. The 400 µl of samples are applied to the strips placed in the apparatus. These are left to rehydrate passively for 1 hour, then actively for 10 hours at 50V/strip, then the programme is started according to the manufacturer's instructions. After focusing, the strips are used or stored at −80° C.

2nd Dimension

Before use, the strips are equilibrated for 30 minutes in a 1-D buffer (50 mM Tris pH 6.8; 10% (v/v) of glycerol; 2% (v/v) of (3-mercaptoethanol; 2% (w/v) of SDS; 0.05% (w/v) of bromophenol blue) then placed on top of a 1-D separation gel of 16.5% acrylamide. The strip is recovered with a 1% agarose solution (w/v). The subsequent method is identical to a single 1-D electrophoresis.

Transfer to Membrane and Immunoblotting

Transfer

The transfer was carried out using the Pharmacia LKB Multiphor® semi-dry transfer system, following the manufacturer's instructions (Amersham-Pharmacia Biotech). The proteins were transferred at 0.8 mA/cm² to a Hybond® ECL nitrocellulose membrane (Pharmacia-Amersham).

Immunoblotting

The membrane is incubated for 60 minutes in buffer (15 mM Tris pH 8.0; 150 mM NaCl; 0.5% (v/v) of Tween®-20) containing 5% (w/v) of skimmed milk then washed with the same buffer without milk containing 0.1% of Tween®-20 instead of 0.5%.

The membrane is incubated for 2 hours at ambient temperature or overnight at 4° C., with the APP-Cter-C17 antibody diluted to a final dilution of $1/2000^{th}$ (v/v) in an incubation buffer (15 mM Tris pH 8.0, 150 mM NaCl, 0.1% (v/v) of Tween-20 and 3% (w/v) of skimmed milk).

The membrane is washed 3 times for 10 minutes in the incubation buffer free from milk.

The membrane is then incubated for 1 hour at ambient temperature, with an anti-rabbit goat immunoglobulin coupled to Raifort's peroxidase, at a final dilution of $1/4000^{th}$ (v/v) in incubation buffer free from milk.

The membrane is washed three times for 10 minutes in incubation buffer free from milk, and the immunoreactive polypeptides are revealed using the ECU) chemiluminescence kit (Pharmacia-Amersham Biotech) according to the manufacturer's instructions.

Results

The theoretical analysis of the catabolic and/or metabolic cleavage of the APP is shown in FIG. 1A and the localization of the epitopes of the antibodies used in FIG. 1B.

1-D Analysis of the Human Cerebral Tissue

Samples of human cerebral tissue, prepared as described in the methodology for a 1-D analysis, were loaded and analyzed. The electrophoretic separation took place under Tris-Tricine conditions as described. Calibrated molecular weight markers (Biorad) were applied in parallel in order to determine the molecular mass of the fragments using ImageMaster® 1-D Elite software (Amersham-Pharmacia Biotech).

Figure 2:
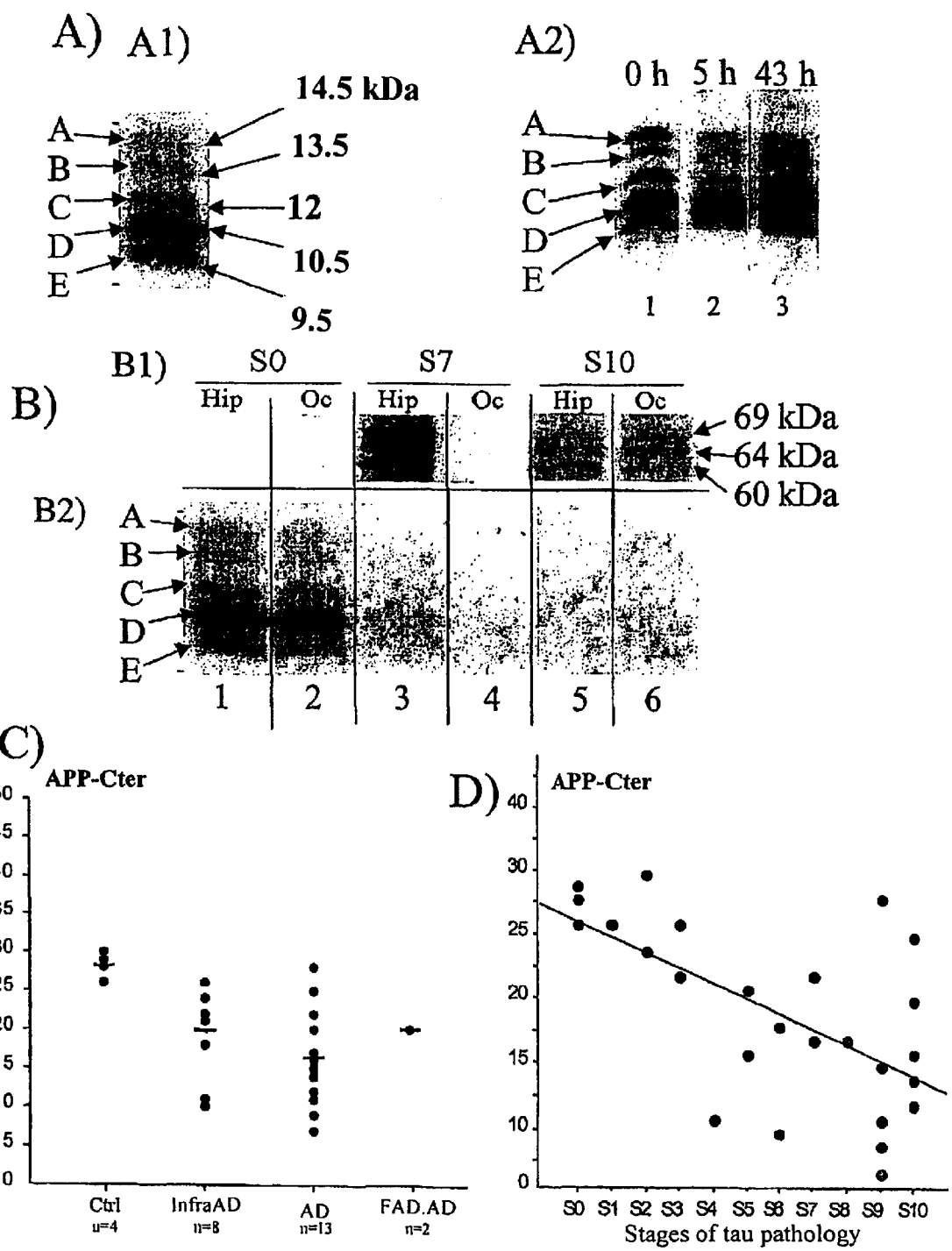

Transfer of the proteins separated by electrophoresis and immunoblotting with the APP-Cter-C17 antibody was carried out as described. The results are represented in FIG. 2, A1.

Analysis of Normal Tissue

In the control human cerebral tissue, six bands designated A, B, C, D and E of apparent molecular masses A 14.5 kDa; B 13.5 kDa; C 12 kDa; D 10.5 kDa; E 9.5 kDa are revealed by the APP-Cter-C17 polyclonal antibody. They are detected in both the human cerebral tissue biopsy and in the post-mortem cerebral tissue of a control subject (FIG. 2, A2; Track 1: biopsy; Tracks 2 and 3: autopsy). The post-mortem period is indicated in hours for each of the samples. It can be noted that the profile of the fragments is not modified during the post-mortem period. The 5 fragments therefore do not result from a catabolic enzymatic activity which can be produced after death.

Analysis of the Tissue from Patients at Different Stages of Alzheimer's Disease.

A) Reduction in the Quantity of APP-Cter Fragments During Alzheimerization

FIG. 2B represents the analysis, on the same samples and the same immunoblots, of the tau pathology according to the classification of Delacourte et al., 1999 (FIG. 2, B1) and APP-Cter fragments (FIG. 2, B2) in a control subject (Tracks 1 and 2) and two patients suffering from Alzheimer's disease (Tracks 3 to 6). Two cerebral regions were studied: the hippocampus (Hip, Tracks 1, 3 and 5) and the occipital cortex (Oc, Tracks 2, 4 and 6). A reduction of the APP-Cter fragments is noted during the disease. This disappearance is correlated with the severity of the neurodegenerative attack. In fact, it can be noted that the APP-Cter fragments disappear (FIG. 2, B2) in the regions affected by the tau pathology, visualized by the presence of the triplet of tau pathological proteins of 69, 64 and 60 kDa (FIG. 2, B1) (Delacourte et al. (6)).

A statistical study of a large number of patients shows the excellent correlation between the progress of the pathological process, revealed by the stages of tau pathology, and the reduction in the quantity of APP-Cter fragments in the samples of cerebral tissue studied.

The quantities of APP-Cter were determined in the cortex of 4 groups of patients: the control cases (Ctrl), the infraclinical cases (infraAD) which correspond to patients without dementia, but with the lesions characteristic of Alzheimer's disease, the clinical cases of Alzheimer's disease (AD) and the familial autosomal dominant cases of Alzheimer's disease (FAD.AD) (FIG. 2, C). The Mann-Whitney non-parametric statistical test indicates a significant reduction between the infraAD and AD groups compared with the controls Ctrl (infraAD: $p<0.03$; AD $p<0.002$). The average APP-Cter reduction is 1.5 times for the infraAD group and 1.7 times for the AD group compared with the control group. The APP-Cter reduction in the infraAD and AD groups is not significantly different. This demonstrates that this APP-Cter reduction is an early event in the Alzheimer physiopathology.

The statistical study of the relationship between the levels of APP-Cter expression with respect to the stages of the tau pathology in the temporal cortex of the control patients and at different stages of Alzheimer's disease was carried out (FIG. 2, D). A significant relation is observed between the APP-Cter quantities detected in the cortex of each patient studied and the different stages of tau pathology, both in the temporal cortex and in the occipital cortex.

| | Linear regression | | |
|---|---|---|---|
| | n | r | p |
| temporal cortex | 26 | 0.614 | 0.0009 |
| occipital cortex | 22 | 0.457 | 0.0324 |

B) Transformation of the APP-Cter Fragments During the Alzheimerization Process

Figure 3:
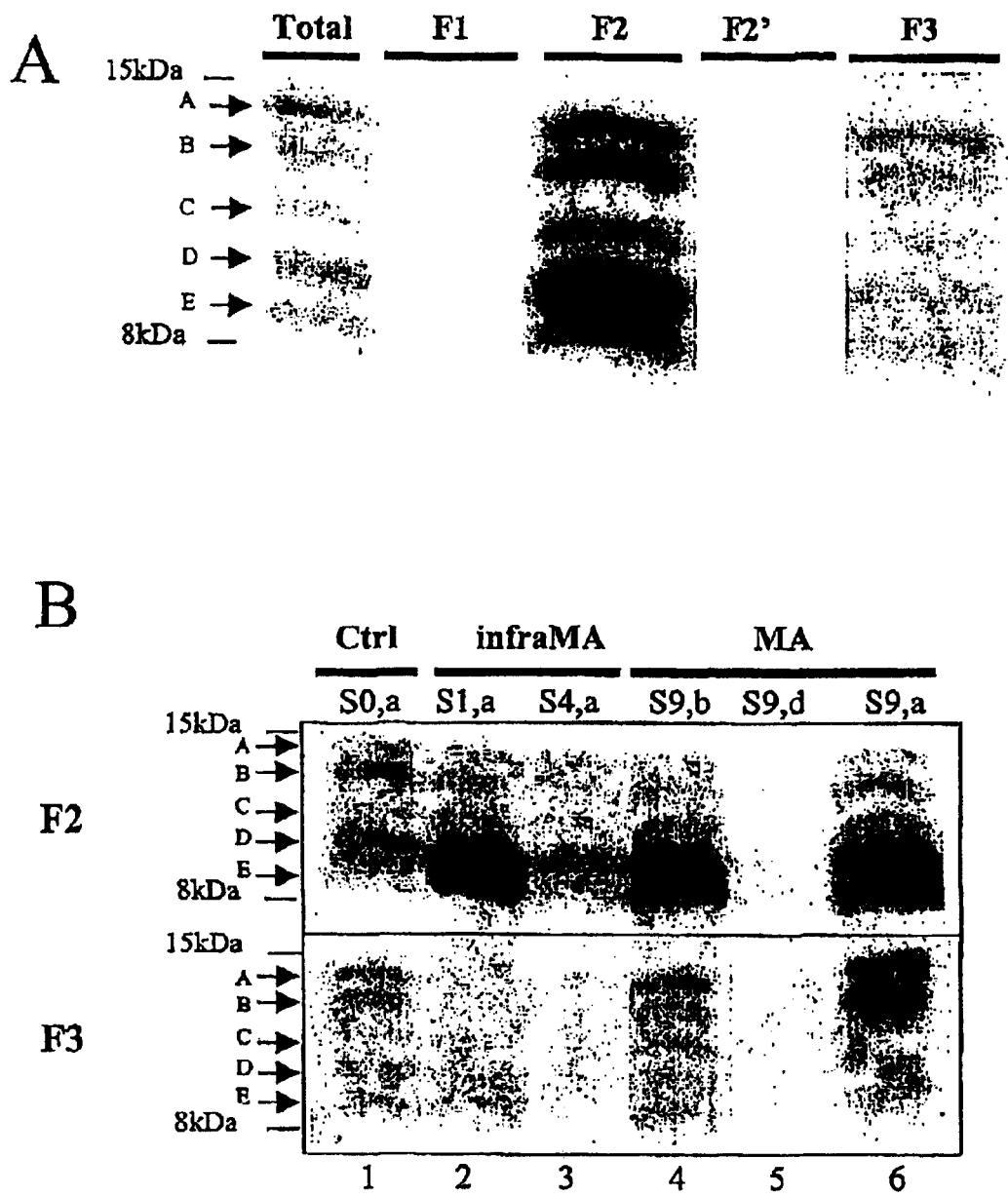

The APP-Cter fragments are preferably extracted in two phases: a buffer solution containing a non-ionic detergent, Triton X100 (F2 fraction), and a solution containing an ionic detergent, sodium dodecyl sulphate (SDS) (F3) (FIG. 3, A).

Differential variations are observed in solubility of the APP-Cter fragments during the Alzheimerization of the cerebral tissue (FIG. 3B). An increase is noted in the solubility of the APP-Cter fragments of molecular mass of 9.5 (Fragment E) and 10.5 kDa (Fragment D) in the F2 fraction and an increase in the insolubility of the APP-Cter fragments of molecular mass of 13.5 (Fragment B) and 14.5 kDa (Fragment A) in the F3 fraction.

2-D Analysis of Normal and Pathological Human Cerebral Tissue

Figure 4:
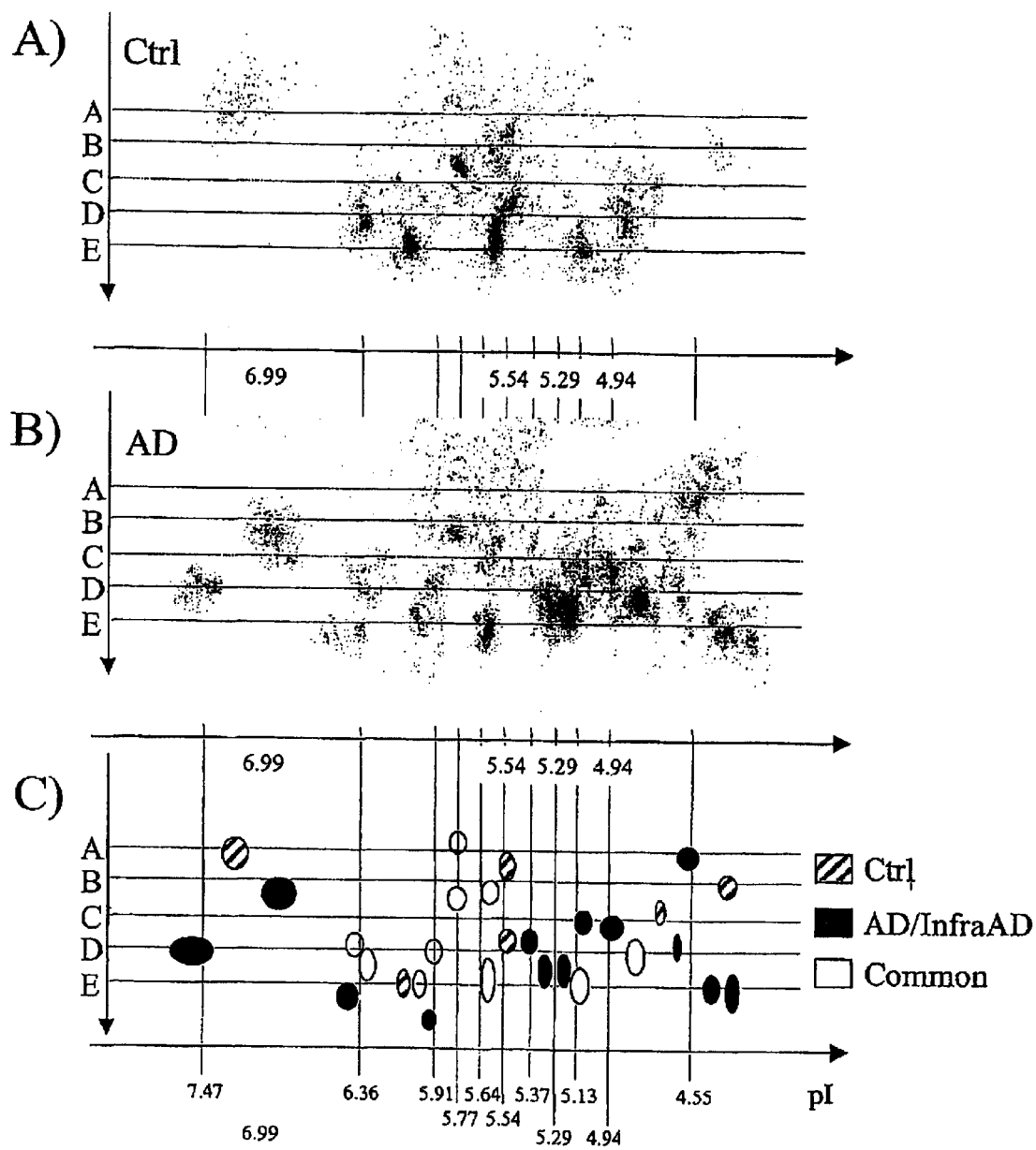

The results for 3 patients are presented in FIG. 4 (A to C).
one control patient, without Alzheimer-type cerebral lesions (Stage 0 according to Delacourte et al., (6)) (FIG. 4A)
one patient at the very start of the clinical phase of Alzheimer's disease, at Stage 6 according to Delacourte et al., (6)) (FIG. 4B).

The arrows indicate the spots detected by the APP-Cter-C17 polyclonal antibody. Their molecular masses are similar to those observed in the 1-D immunoblots. The isoelectric points are included in the pH range from 4.5 to 7.5.

A modification can be noted in the distribution of the spots during the development of Alzheimer's disease (FIG. 4, C). The patients at a more advanced stage of Alzheimer's disease could not be studied by this approach, since the fragments can no longer be detected.

The APP-Cter variants detected by 2D analysis are represented diagrammatically (FIG. 4, C) on a grid calibrated in two dimensions, the Y axis representing the molecular masses and the X axis the isoelectric points. The whole was calibrated with internal molecular mass and isoelectric point controls. The isoelectric point controls are gamma-enolase (47/4.94), alpha-actin (42/5.29) and alpha-enolase (47/6.99). The isoelectric points at 5.54 and 8.05 are internal cerebral tissue standards.

The diagram in FIG. 4 represents the superposition of the 2D profiles of the APP-Cter fragments detected with the APP-Cter-C17 antibody in the human cerebral tissue of a control subject and of Alzheimer's patients at the infraclinical stage of the disease and at the start of the clinical stage of Alzheimer's disease. The spots, i.e. the different 2-D isoelectric variants, observed both in the healthy and pathological tissue are represented by empty circles. The spots specific to the healthy tissue are represented by circles with a hatched background and those specific to the Alzheimerized tissue by a black background.

The values of the molecular masses and the isoelectric points of the spots modified during Alzheimer's pathology are shown in Table 1.

1-D Analyses of the Murine Cerebral Tissue

In order to better characterize the specificity of the catabolism and/or metabolism of the human APP, the APP-Cter products were analyzed (in the same manner as in the human cerebral tissue) in a rat and non-transgenic mice but also in transgenic mice for the wild-type human APP gene (APPwt) or carrying the Swedish mutation (APPsw). FIG. 5A represents the immunomarking of the APP-Cter fragments of the control, and transgenic, mice, compared with the profile of the human cerebral tissue (FIG. 5A, Track 4).

Identical deposits of the homogenates of cerebral tissue were introduced into each electrophoresis well. The APP-Cter fragments were detected with the APP-Cter-C17 polyclonal antibody. Track 1 of FIG. 5 corresponds to the analysis of the non-transfected mouse (negative control), Track 2 corresponds to the mouse with a single copy of the APPwt human gene, Track 3 corresponds to the transgenic mouse with the APPsw human mutated gene, and Track 4 corresponds to control human cerebral tissue. The arrows indicate the molecular masses of the electrophoretic bands detected.

It can be noted that the control mice or those with a single copy of the APPwt gene essentially synthesize 4 APP-Cter fragments, whereas the mice with the APPsw gene and the normal human cerebral tissue synthesize 5 APP-Cter fragments, with a molecular mass of 14.5; 13.5; 12; 10.5 and 9.5 kDa.

These results were verified on 5 non-transgenic mice, 2 transgenic mice with the wild-type human APP gene and 5 transgenic mice with the APPsw gene.

Figure 5:
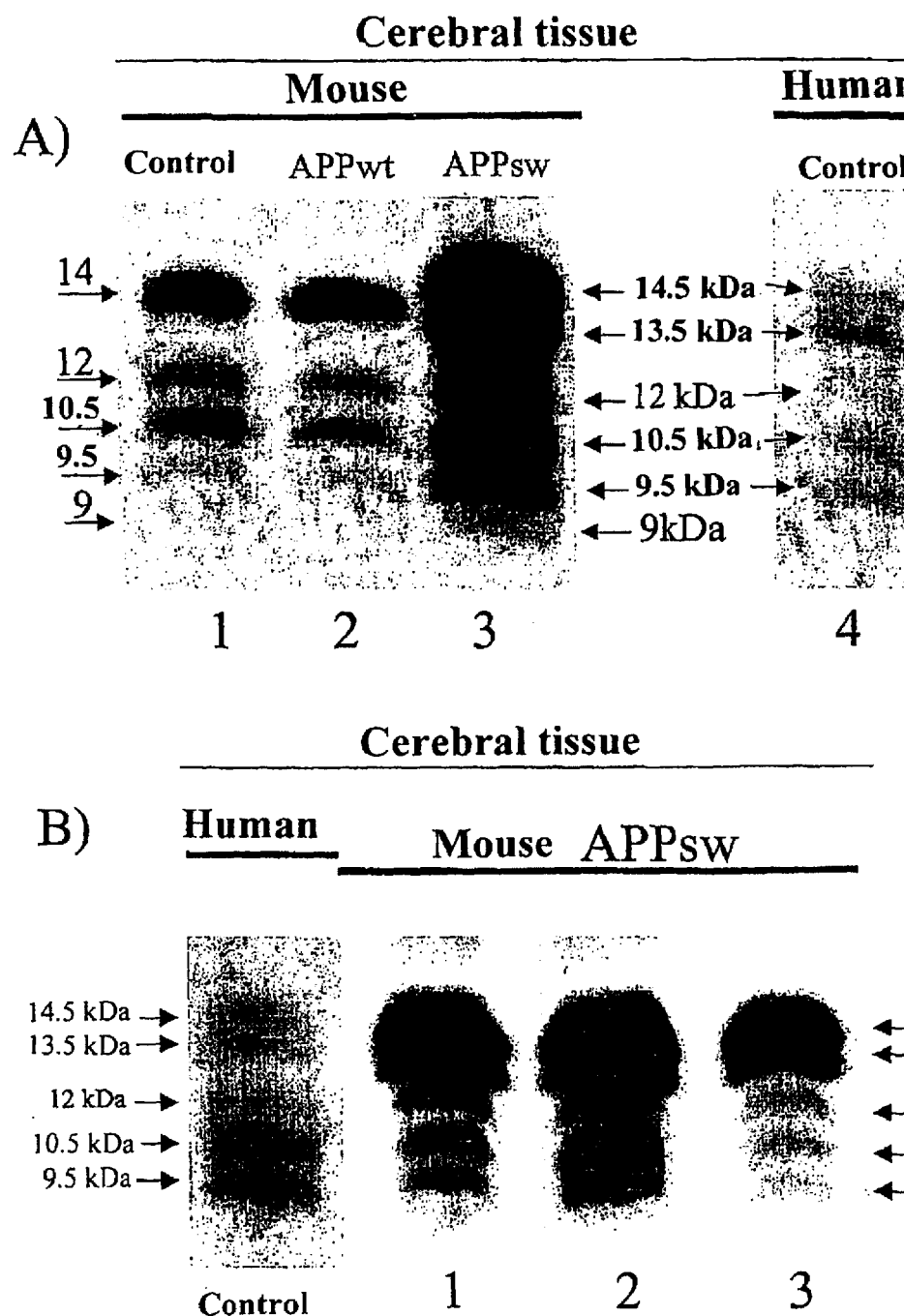
Figure 7:
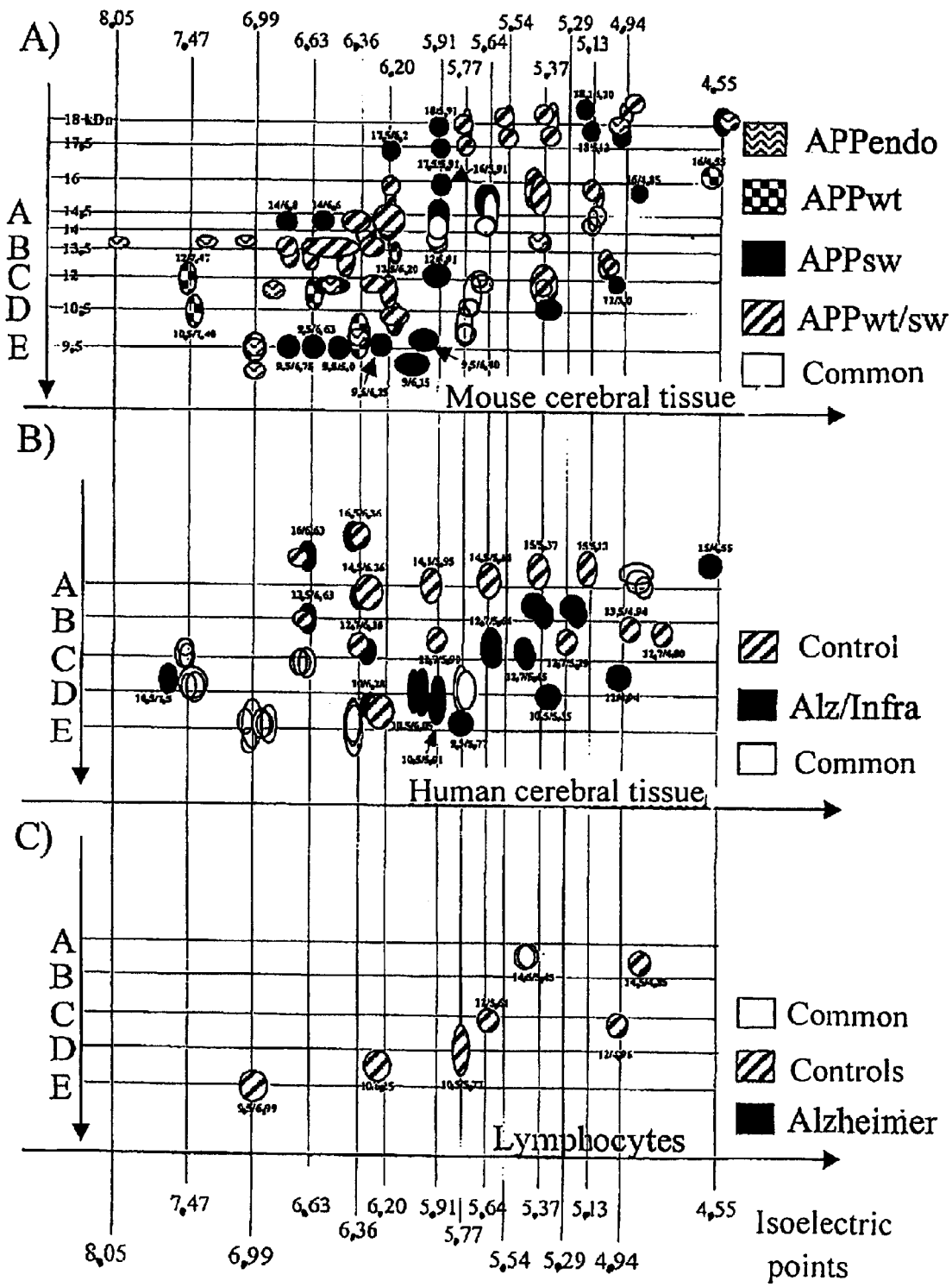

FIG. 5B, Tracks 1 to 3, shows the results of immunoblotting with the APP-Cter-C17 antibody on different APPsw transgenic mouse lines (FIG. 5, Tracks 1 to 3), among which is found (Track 3) the reference APPsw line described by Hsiao et al., (8). The APPsw transgenic mice therefore systematically possess a particular profile, as described here.

2-D Analysis of the APP-Cter Fragments of Mouse Cerebral Tissue

An operation as described above for human cerebral tissue (FIG. 4) is carried out. It is therefore possible to characterize the different variants observed in the control mouse (FIG. 6A), the APPwt mouse (FIG. 6B) and the APPsw mouse (FIG. 6c). An increase can be noted in the expression of the variants for the APPsw mice and a modification of the profile for certain variants (FIG. 6). The molecular mass and isoelectric point values are shown in FIG. 7a and Table 3.

1-D Analysis of the Modifications of Human APP in Cellular Models

Non-Neuronal Models

Figure 8:
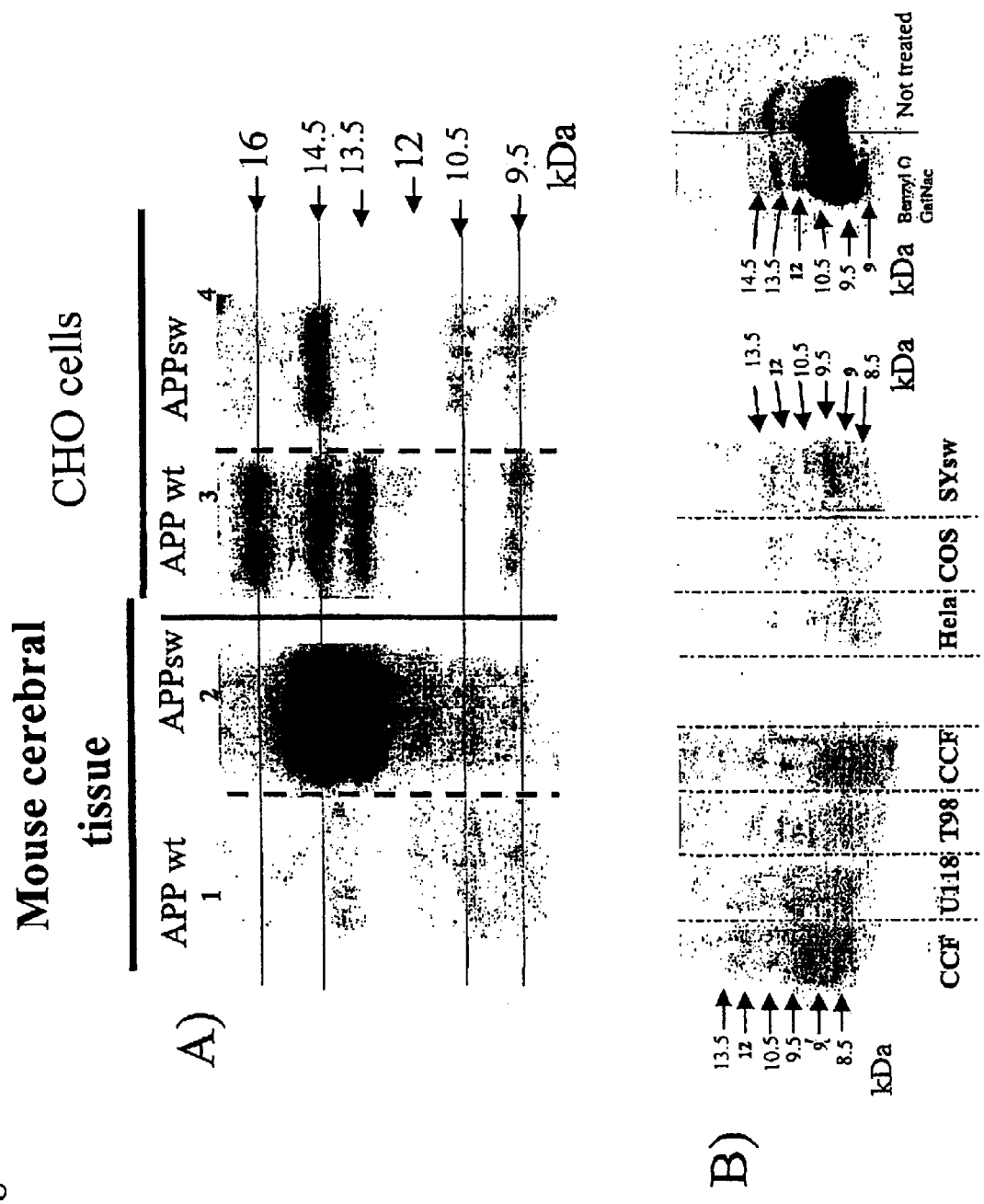

CHO (Chinese Hamster ovarian) cells, transfected in a stable manner with the wild-type human APP gene (APPwt) or the APPsw gene, were analyzed according to the protocol described. The results in FIG. 8 show the APP-Cter fragments of the CHO cells, in comparison with the cerebral tissue from transgenic mouse with the APPwt or APPsw gene.

In the APPwt CHO cells (FIG. 8, Track 3), 6 bands of apparent molecular masses of 16; 14.5; 13.5; 12; 10.5 and 9.5 kDa are detected. The major bands are the 16; 14.5; 13.5; and 9.5 kDa bands. In the APPsw CHO cells (FIG. 8, Track 4), a reduction in the overall signal is observed, especially of the 16; 13.5; and 9.5 kDa fragments.

Comparison with the homogenates of APPwt (Track 1) and APPsw (Track 2) transgenic mouse cerebral tissue indicates that the bands detected in the CHO's are common to those of the cerebral tissue, except for the 16 kDa band.

It is noted that the CCF, U118 and T9 glial cell strains possess a profile with 6 bands, of 13.5, 12, 10.5, 9.5, 9 and 8.5 kDa, with an abundance of the 3 bands between 9.5 and 8.5 kDa (FIG. 8B). A similar profile is observed in Hela, COS and SY-5Y cell strains transfected with the APPsw (FIG. 8B).

Moreover, the HT-29 epithelial cell strain has a profile with 6 bands of 14.5, 13.5, 12, 10.5, 9.5 and 9 kDa (FIG. 8: HT-29). The 9 kDa band which is discrete in the HT-29 epithelial cells becomes more abundant after treatment by benzyl-O-GalNac which inhibits glycosylation and the orientation of the glycosylated proteins. This demonstrates that the glycosylation is a post-translational modification which regulates the APP-Cter expression and profile. This modification is therefore an important element to take into account in research into APP-Cter molecular pathological transformations during Alzheimerization.

Neuronal Models

Figure 9:
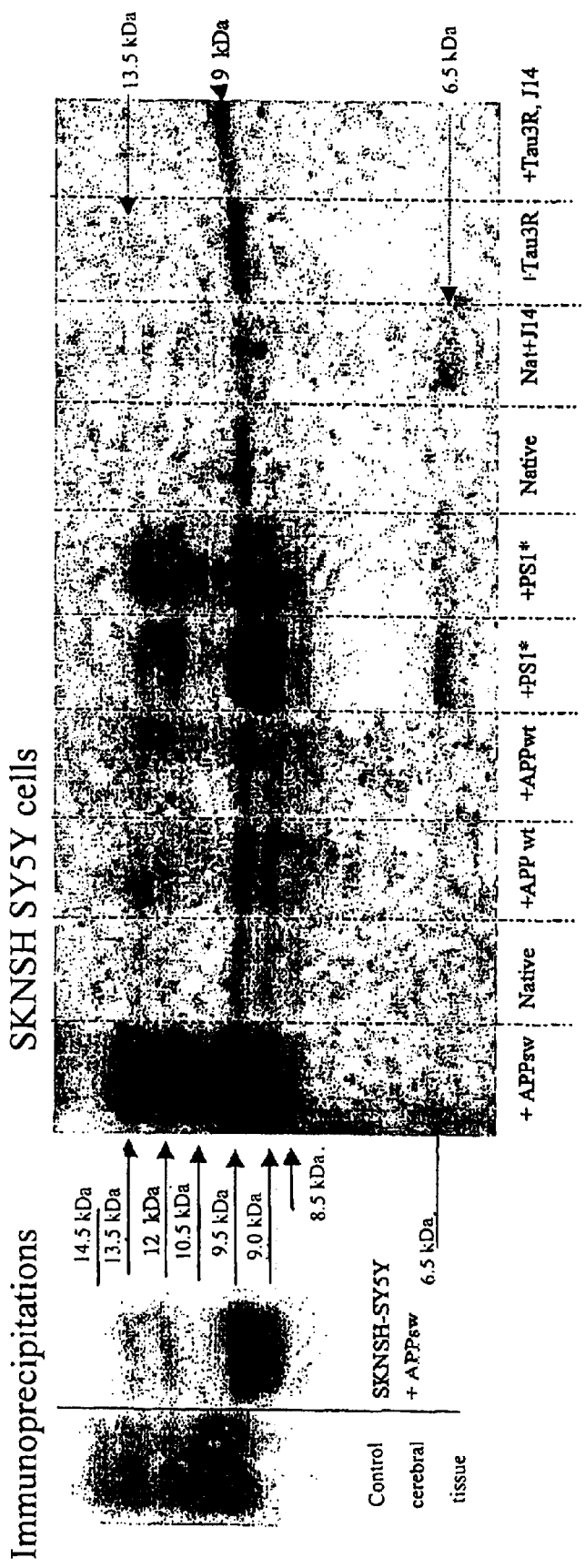

Human neuroblastoma cells (SKNSH-SY5Y) transfected, in a stable fashion, with the APPsw, APPwt, mutated PS1 and Tau genes were analyzed in comparison with non-transfected cells. The results are represented in FIG. 9. In the non-transfected cells, the APP-Cter signal corresponds to the 10.5 kDa band (FIG. 9: Native). On the other hand, 6 fragments of 13.5, 12, 10.5, 9.5, 9 and 8.5 kDa are perfectly identifiable in the non-differentiated SKNSH cells, transfected with APPsw (FIG. 9: APPsw). The 6-band profile is also found with the cells transfected with APPwt (FIG. 9: wild type). The transfection of the SY5Y cells with the mutated PS1 gene causes an increase in the 5 bands, the 9.5 kDa band which is abundant here, and also the 6.5 kDa fragment, released by the gamma secretase activity.

Other native neuronal lines also possess profiles of the native SKNSH type, such as the Kelly cells, or, moreover, such as the SKNSH cells transfected with a mutated APP or PS1 gene, such as the NT2 and hNT cells.

Differentiation over 14 days of the SY5Y cells causes a change in profile, with the appearance of the 6.5 kDa gamma band, and a reduction of the 10.5 kDa band. Under the same conditions, the cells transfected with the 3R tau gene, and non-differentiated, see the appearance of the 13.5 kDa band, corresponding to an increase in the release of the "beta secretase" fragments. In these differentiated cells, the disappearance of the 6.5 kDa gamma band is observed.

This demonstrates that genes are capable of modulating the expression and relative distribution of the APP-Cter fragments. These models therefore have the potential to model the pathological modifications of the APP-Cter fragments, as observed in the human cerebral tissue.

Analysis of the APP-Cter Fragments of the Human Leukocytes

Pellets of human leukocytes were prepared according to a standard protocol used in the analysis laboratory (medical or hospital). These pellets were treated as described and analyzed by immunoblotting with the APP-Cter-C17 antibody. The results are shown in FIG. 10A where Tracks 1 to 5 correspond to the controls and Tracks 6 to 11 to samples originating from patients suffering from Alzheimer's disease. Sex and age are mentioned (FIG. 10A: sex.age).

The APP-Cter-C17 antibody detects three fragments with a molecular mass of 14 kDa, 10.5 kDa and 9.5 kDa.

A comparative 1-D analysis of leukocytes from control subjects and patients diagnosed with Alzheimer's disease makes it possible to demonstrate (as in the human cerebral tissue study) a reduction in the APP-Cter fragments in the leukocytes of the patients (Tracks 6 to 11) compared with the leukocytes of control subjects (Tracks 1 to 5).

The variants of the APP-Cter fragments of the leukocytes have also been analyzed in 2D (FIG. 10B). The molecular mass and isoelectric point values of each spot detected are shown in FIG. 7C and Table 2.

Characterization of the APP-Cter Fragments with Different Immunological Probes

An antibody to the N-terminal end of the Aβ peptide makes it possible to localize the cleavage fragment of the beta-secretase. This is the FCA18 antibody (4). The 14 kDa fragment of the leukocytes is detected by this antibody, indicating that it is the APP-Cter fragment produced by the beta secretase (FIG. 11B). In the cerebral tissue, the two bands A (14.5 kDa) and B (13.5 kDa) are recognized by WO2, a monoclonal antibody (Abeta, GmbH, Heidelberg, Germany) to the 5-11 part of the Aβ peptide, while band B is detected by FCA18, which indicates that bands A and B are generated by a cleavage situated at the level of the beta secretase region (see FIG. 1). Moreover, database interrogation (SwissProt, for example) indicates that the APP-Cter fragment with a molecular mass of 9.5 kDa (FIG. 11) and isoelectric point of 6.99 corresponds to the alpha-secretase fragment, as represented in FIG. 1. The two major APP-Cter fragments of the leukocytes which are modified during Alzheimer's disease have therefore been identified (FIG. 11, A and B).

Moreover, certain sites common to the 5 fragments A to C can be modified differentially. Thus, for example, a polyclonal antibody specifically recognizing phosphorylated threonine 668 preferentially recognizes bands A, C and D. The method described here makes it possible to characterize the post-translational modifications linked to the degenerative process. It therefore leads to the possibility of developing new immunological tools which will advantageously lead to the diagnostic kit for the pathological transformation of the APP-Cter fragments.

The Phosphorylation of the APP-Cter Fragments is a Determining Element in their Pathological Transformation A modification of the APP-Cter metabolism and phosphorylation occurs in Alzheimer's disease. The APP-Cter's of the cerebral tissue of a control subject and an Alzheimer's patient were immunoprecipitated using the APP-Cter-C17 antibody and the 5 fragments of 14.5, 13.5, 12, 10.5 and 9.5 kDa (fragments A, B, C, D and E) are revealed after electrophoresis in Tris-Tricine gel with the same antibody (FIG. 13, Tracks 1 and 2). The immunoprecipitated APP-Cter fragments were dephosphorylated using calf intestine alkaline phosphatase (FIG. 13, Tracks 3 and 4), then revealed with the APP-Cter-C17 antibody following the same protocol. Three major fragments are detected in the control homogenate, of 13.5, 10.5 and 9.5 kDa. These three fragments are also detected in the Alzheimer's homogenate. However, the 13.5 kDa fragment is in a smaller quantity whereas the 10.5 and 9.5 kDa fragments are in a greater quantity. This result shows the accumulation of the fragments generated by the alpha-secretase cleavage, but also their greater phosphorylation.

The modifications of the phosphorylation index are demonstrated in particular with the anti-phosphorylated threonine 668 antibody (FIG. 13, Tracks 5 and 6). The APP-Cter fragments phosphorylated on the Threonine 668 were immunoprecipitated and revealed using the APP-Cter-C17 antibody after electrophoresis in Tris-Tricine gel. The 14.5; 12 and 10.5 fragments are detected in the control homogenate. In the Alzheimer's homogenate, it is essentially the 12.5 and 10.5 fragments which are detected in large quantities. This result confirms that the APP-Cter fragments C and D are more phosphorylated and in greater quantity in the early phase of Alzheimer's disease, and that in parallel, fragment A is not, or only slightly, phosphorylated at the site 668.

SUMMARY

Particularly informative variants for the implementation of the invention are shown in the summary tables (FIGS. 14 to 16). These different variants constitute markers which are very useful for detecting the pathological modifications of the APP, both in the neuronal tissues and in the non-neuronal tissues, and in particular the lymphocytes.

The phosphorylation on the threonines, serines and tyrosines of the APP-Cter fragments (FIG. 1) contributes to the general profile of the APP-Cter's. In the first place, a difference is observed in the phosphorylation index of these different APP-Cter fragments, as shown in particular by the phosphorylated threonine 668 (FIGS. 11 and 13). Then the profile of the dephosphorylated APP-Cter fragments is modified, with, in particular, the disappearance of the 14.5 kDa band, and the new profile then resembles that of the SKNSH cellular models transfected with APPsw (FIG. 13).

The dephosphorylation of the APP-Cter fragments moreover reveals a change in profile between normal tissue and Alzheimer's tissue, with in particular an accumulation of bands C, D, E, of the APP-Cter fragments, corresponding to the alpha-secretase cleavage products (FIG. 13). The dephosphorylation is therefore an important post-translational event, and a marker of the pathological transformation of the APP-Cter fragments.

This modification is also reflected in the gamma-secretase fragment, of 6.5 kDa, which is modified in its expression by the genes involved in Alzheimer's disease, as shown by the cellular models (FIG. 9).

The detection of the APP-Cter fragments allows the definition of a pathological transformation index, applicable to neuronal human tissue (FIG. 12A: human cerebral tissue) or non-neuronal human tissue (FIG. 12B: human lymphocytes), as well as experimental, animal (FIG. 12C: cerebral tissue from APPsw and wt transgenic mice) or cellular, neuronal (FIG. 12D: neuroblastoma cells) or non-neuronal (CHO cells, COS, etc.) models. This index varies from 0 (healthy tissue) to 100% (Alzheimerized pathological tissue) (FIG. 12).

REFERENCES

1. De Strooper B, Konig G (1999) Alzheimer's disease. A firm base for drug development [news] [comment]. *Nature*, 402, 471-2.
2. Sigurdsson E M, Permanne B, Soto C, Wisniewski T, Frangione B (2000) In vivo reversal of amyloid-beta lesions in rat brain. *J Neuropathol Exp Neurol*, 59, 11-7.
3. Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P. (1999) Immunization with amyloid-beta attenuates Alzheimer-disease-like pathology in the PDAPP mouse. *Nature* 400:173-7.
4. Ancolio K, Dumanchin C, Barelli H, Warter J M, Brice A, Campion D, et al. (1999) Unusual phenotypic alteration of beta amyloid precursor protein (betaAPP) maturation by a new Val-715→Met betaAPP-770 mutation responsible for probable early-onset Alzheimer's disease. *Proc Natl Acad Sci USA*, 96, 4119-24.
5. Vaitukaitis J, Robbins J B, Nieschlag E, Ross G T (1971) A method for producing specific antisera with small doses of immunogen. *J Clin Endocrinol Metab*, 33, 988-91.
6. Delacourte A, David J P, Sergeant N, Buee L, Wattez A, Vermersch P, et al. (1999) The biochemical pathway of neurofibrillary degeneration in aging and Alzheimer's disease, *Neurology*, 52, 1158-65.
7. Duff K, Eckman C, Zehr C, Yu X, Prada C M, Perez-tur J, et al. (1996) Increased amyloid-beta42(43) in brains of mice expressing mutant presenilin 1. *Nature*, 383, 710-3.
8. Hsiao K, Chapman P, Nilsen S, Eckman C, Harigaya Y, Younkin S, et al. (1996) Correlative memory deficits, Abeta elevation, and amyloid plaques in transgenic mice. *Science*, 274, 99-102.
9. Laemmli U K (1970) Cleavage of structural proteins during the assembly of the head of bacteriophage T4. *Nature*, 227, 680-5.
10. Schagger H, von Jagow G (1987) Tricine-sodium dodecyl sulfate-polyacrylamide gel electrophoresis for the separation of proteins in the range from 1 to 100 kDa. *Anal Biochem*, 166, 368-79.

We claim:

1. A method for diagnosing a patient for Alzheimer's Disease comprising detecting a pathological modification of an endogenous Amyloid Precursor Protein in a sample from said patient, by assaying the sample for a reduction in the quantity of markers and/or for a change in charge or isoelectric point of the markers and/or for a change in solubility of the markers, wherein said markers are selected from the group consisting of catabolic and/or metabolic fragments of the carboxy-terminal portion of Amyloid Precursor Protein.

2. The method of claim 1, wherein said markers are selected from the group consisting of fragments of the carboxy-terminal portion of Amyloid Precursor Protein of 14.5 kDa; 13.5 kDa; 12 kDa; 10.5 kDa; 9.5 kDa; 9 kDa; 6.5 kDa; and isovariants of isoelectric focusing of those fragments, and combinations thereof.

3. The method of claim 1, wherein said sample is assayed for 1 to 8 fragments chosen from among those of 14.5 kDa; 13.5 kDa; 12 kDa; 10.5 kDa; 9.5 kDa; 9 kDa; 8.5 kDa; 6.5 kDa, and isovariants of isoelectric focusing of those fragments, and combinations thereof.

4. The method of claim 1, wherein the assay analyzes a reduction in the quantity of markers.

5. The method of claim 4, wherein said sample is assayed for a marker selected from the group consisting of fragments of the carboxy-terminal portion of Amyloid Precursor Protein of 14.5 kDa; 13.5 kDa; 12 kDa; 10.5 kDa; 9.5 kDa, and isovariants of isoelectric focusing of those fragments, and combinations thereof.

6. The method of claim 5, further comprising assaying the sample for a fragment of Amyloid Precursor Protein of 6.5 kDa and isovariants of isoelectric focusing of those fragments.

7. The method of claim 5, further comprising assaying the sample for a fragment of Amyloid Precursor Protein of 9 kDa and isovariants of isoelectric focusing of that fragment.

8. The method of claim 4, wherein said sample is assayed for 8 fragments of Amyloid Precursor Protein of 14.5 kDa; 13.5 kDa; 12 kDa; 10.5 kDa; 9.5 kDa; 9 kDa; 8.5 kDa; and 6.5 kDa; and isovariants of isoelectric focusing of those fragments.

9. The method of claim 1, wherein the charge or isoelectric point of the markers is determined.

10. The method of claim 9, wherein the assay detects a modification of phosphorylation of Amyloid Precursor Protein.

11. The method of claim 10, wherein the sample is analyzed for phosphorylation of β-stubs (bands A, B).

12. The method of claim 10, wherein the sample is analyzed for an increase in phosphorylation of α-stubs (band C, D, E).

13. The method of claim 1, wherein the sample is also analyzed for the solubility of the markers.

14. The method of claim 13, wherein the sample is analyzed for a reduction in the solubility of fragments of 14.5 kDa and/or 13.5 kDa.

15. The method of claim 13, wherein the sample is analyzed for an increase in the solubility of fragments of 10.5 kDa and/or 9.5 kDa.

16. The method of claim 1, wherein the samples to be analyzed comprise neuronal tissues or cells, or non-neuronal tissues or cells.

17. The method of claim 1, wherein said assay is performed using a polyclonal and/or monoclonal antibody to the carboxy-terminal region of Amyloid Precursor Protein.

18. The method of claim 17, wherein said assay is performed using a set of polyclonal and/or monoclonal antibodies that reveal post-translational modifications of a pathological transformation of the carboxy-terminal fragments of Amyloid Precursor Protein.

19. The method of claim 18, wherein the assay is performed using polyclonal and/or monoclonal antibodies that permit assessment of relative phosphorylation and variation of expression of the 14.5 kDa; 12 kDa and 10.5 kDa fragments.

20. The method of claim 1, wherein the pathological modification is evaluated by allocating an index to the fragments identified in the sample studied, this index being assigned with respect to a system of reference where the index 0 (zero) corresponds to detection in healthy tissue, and the index 100 (one hundred) in pathological tissue.

21. The method of claim 1, wherein the pathological modification is associated with a neurodegenerative disease.

22. The method according to claim 21, wherein the neurodegenerative disease is Alzheimer's disease.

23. The method of claim 22, wherein the pathological modification is detected in cell culture or in an animal model.

24. The method of claim 23, wherein the detection of the pathological condition is done in the presence of a molecule to assess the effectiveness of the molecule against neurodegenerative pathologies.

25. The method of claim 22, wherein the detection of Alzheimer-type neurodegenerative pathologies is made on human tissue.

26. The method of claim 1, further comprising the step of monitoring and/or correcting a therapeutic treatment based on the catabolism and metabolism of Amyloid Precursor Protein.

* * * * *